United States Patent [19]
Reed et al.

[11] 3,944,261
[45] Mar. 16, 1976

[54] BIFURCATED TUBING CONNECTOR

[75] Inventors: Charles C. Reed, Houston; Russell G. Sharp, Sugar Land; Denton A. Cooley, Houston, all of Tex.

[73] Assignee: Texas Medical Products, Inc., Houston, Tex.

[22] Filed: Mar. 5, 1975

[21] Appl. No.: 555,749

[52] U.S. Cl............. 285/21; 29/157 R; 128/214 R; 156/73.1; 285/93; 285/137 R; 285/155; 285/177; 285/DIG. 16
[51] Int. Cl.[2] ........................................ F16L 47/02
[58] Field of Search. 285/155, 137 R, 152, DIG. 16, 285/423, 177, 21, 260, 286; 128/247, 214 R, 214 B, 348; 29/157 R; 156/73.1, 73.2, 294; 428/36

[56] References Cited
UNITED STATES PATENTS

| | | | |
|---|---|---|---|
| 967,483 | 8/1910 | Andrews | 285/155 X |
| 2,183,614 | 12/1939 | Henry | 285/177 X |
| 2,505,303 | 4/1950 | Randa | 285/155 |
| 3,254,153 | 5/1966 | Kohler | 285/137 R |
| 3,552,778 | 1/1971 | Muller | 285/260 X |
| 3,654,965 | 4/1972 | Gramain | 285/137 R X |
| 3,814,103 | 6/1974 | Fettel et al. | 128/348 X |

FOREIGN PATENTS OR APPLICATIONS

| | | | |
|---|---|---|---|
| 178,625 | 4/1922 | United Kingdom | 285/177 |

*Primary Examiner*—Thomas F. Callaghan
*Attorney, Agent, or Firm*—H. Ross Workman; J. Winslow Young

[57] ABSTRACT

An apparatus and method of assembly for a bifurcated tubing connector which is assembled from a relatively small number of integrated parts. The connector includes a tapered, hollow body and cover with standardized fittings. Each fitting is formed of modular components and configured to receive a coupling which accommodates attachment to a different tubing diameter so that the bifurcated connector of this invention may be used to join two tubes of different diameters into a common fluid stream.

7 Claims, 2 Drawing Figures

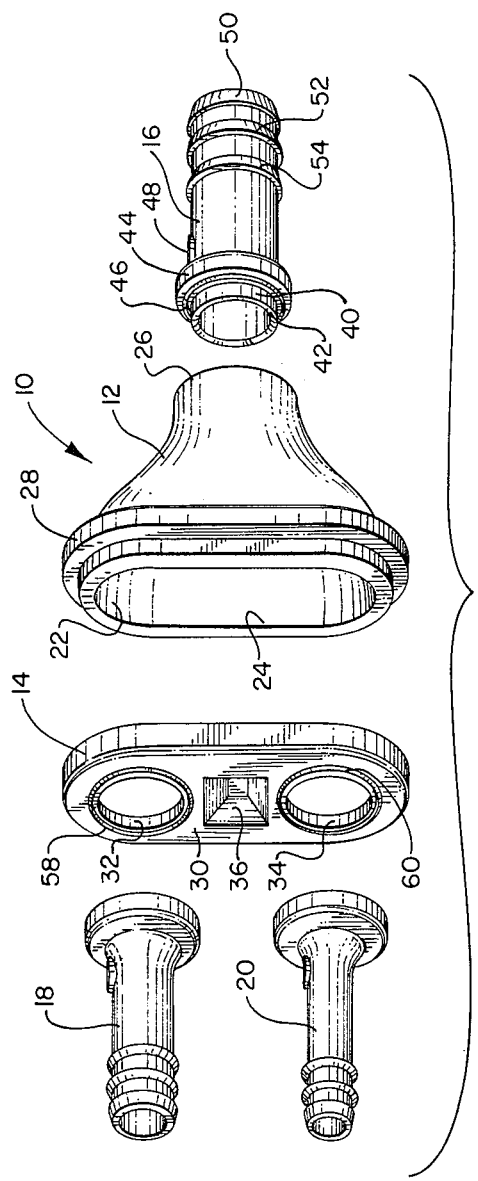
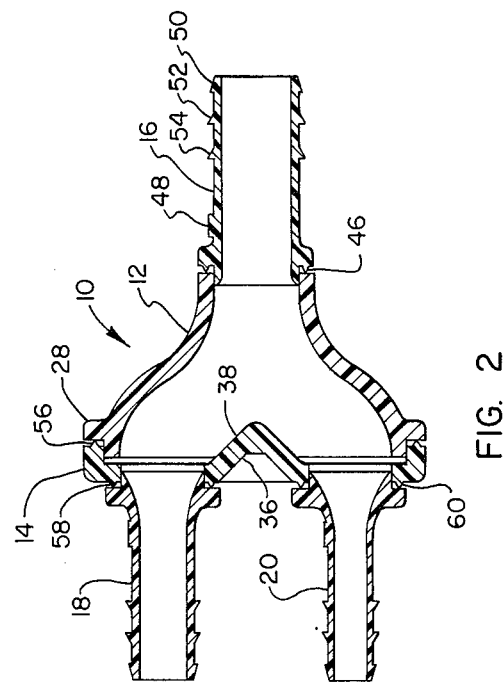

BIFURCATED TUBING CONNECTOR

BACKGROUND

1. Field of the Invention

This invention relates to a bifurcated tubing connector apparatus and method of assembly.

2. The Prior Art

Extracorporeal blood handling systems are well known in the art and are used for numerous applications including, for example, hemodialysis, blood oxygenators, etc. In a number of applications, it is necessary to join two extracorporeal blood lines into a single blood line. Tubing connectors are commercially available and include, for example, a "Y" connector and a "T" connector with two legs of the "Y" or "T" serving as incoming streams with the third leg or stem serving as the outgoing or combined stream.

Each of these prior art connectors pose serious problems inherent in their design in that they tend to subject the blood to hemolytic trauma. For example, blood hemolysis results when blood and its components are exposed to excessive turbulence, sharp corners and obstruction. Additionally, prior art connectors have also been constructed such that dead areas exist in the flow channels which results in blood stagnation and desirable mixing is inhibited by laminar flow.

It is well known that the fluid conduit used to carry blood for bypass, transfusion and the like are supplied in a wide variety of diameters. Heretofore, it has been difficult if not impossible to join tubes having different diameters into a combined stream using a single connector. Resolution of this problem would require a wide variety of connectors from a corresponding number of dies.

It would therefore be an advancement in the art to provide a tubing connector apparatus and method which permits fabrication of a wide variety of connectors from a relatively small number of modular parts from corresponding dies, thereby providing greater flexibility and efficiency in manufacture. The tubing connector should be readily disposable to eliminate the dangers of cross infection and should also be designed so as to minimize hemolysis of blood. Such a tubing connector and method is disclosed herein.

BRIEF SUMMARY AND OBJECTS OF THE INVENTION

The present invention is a bifurcated tubing connector which is assembled from three basic modular parts, (1) a hollow, tapered body, (2) a contoured cover for the enlarged end of the hollow tapered body, and (3) tubing couplings configured to mate with standardized fittings in both the cover and the body. Each of the standard fittings receives a corresponding adapter on each tubing coupling. Preferably, the two standardized fittings of the cover are in the same planar surface to support the tubing couplings of the cover in a parallel relationship and thereby introduce the blood flow into the body as parallel streams. One end of each tubing coupling is configured as a standardized counterpart which mates with a corresponding standardized fitting in either the cover or the hollow body. The other end of the tubing coupling is configured to telescopically receive a tubing of predetermined diameter in mating relationship.

Modular construction of the body, cover, and tubing couplings means that only one die is required for each of the body and cover and for each diameter tubing coupling. Thus a wide range of bifurcated tubing connectors may be fabricated from a relatively small number of components.

The adjoining interior surfaces of each of the hollow body, cover and tubing couplings are all configurated so as to present a smooth flow profile to the blood or other fluid passing therethrough. This feature coupled with the foregoing feature of introducing the blood into the hollow body through parallel flow streams reduces hemolysis of blood.

It is therefore an object of this invention to provide improvements in bifurcated tubing connectors.

Another object of this invention is to provide a tubing connector having a standard sized hollow body and cover therefor which are adapted to receive a variety of tubing couplings for connecting tubing of different diameters.

It is another object of this invention to provide a bifurcated tubing connector which may be assembled from a relatively small number of modular component parts to thereby provide a relatively large number of bifurcated tubing connectors adapted to couple tubings of different sizes.

It is even a still further object of this invention to provide a method for assembling bifurcated tubing connectors from modular parts.

It is an even still further object of this invention to provide a bifurcated tubing connector wherein the tubing couplings are initially interchangeable and are coordinated to mate with standardized openings in the body and cover of the bifurcated tubing connector.

These and other objects and features of the present invention will become more fully apparent from the following description and appended claims taken in conjunction with the accompanying drawing.

BRIEF DESCRIPTION OF THE DRAWING

FIG. 1 is an exploded perspective view of one preferred embodiment of a bifurcated tubing connector of the present invention; and FIG. 2 is a cross-section of the bifurcated tubing connector of FIG. 1 as assembled prior to bonding.

DETAILED DESCRIPTION OF THE PREFERRED EMBODIMENTS

The invention is best understood by reference to the drawing wherein like parts are designated with like numerals throughout.

Referring to the drawing, a bifurcated tubing connector is shown generally at 10 and includes a tapered, hollow body 12, a cover 14 and three tubing couplings indicated herein as couplings 16, 18 and 20, respectively.

The tapered hollow body 12 is, preferably, injection molded from a medical grade plastic and is formed so as to present a smoothly contoured internal surface 22, the function of which will be discussed more fully hereinafter. The hollow body 12 has an oblong or elongated opening 24 and tapers to a standard fitting 26, the function of which will be discussed more fully hereinafter with respect to each of the couplings 16, 18 and 20. Offset from and circumferentially extending around the opening 24 of body 12 is a shoulder 28 which cooperates in abutting relationship with the periphery of cover 14.

Cover 14 is configurated to completely enclose opening 24, the periphery of cover 14 abutting shoulder 28.

Cover 14 includes an essentially planar body 30 having two spaced annular fittings 32 and 34 therein. If desired, each fitting may be provided with concentric ridges or energy directors 58 and 60, respectively, to facilitate ultrasonic welding as will become subsequently more apparent.

Joinder of cover 14 with body 12 creates a universal union which may then receive selected modular couplings so as to form the tubing connector 10. The combination of cover 14 with body 12 is a universal union in that each of fittings 26, 32 and 34 have the same diameter so as to interchangeably receive any one of the modular couplings 16, 18 or 20 at any position. A wedge-shaped depression 36 between fittings 32 and 34 forms a corresponding protrusion 38 on the opposite side of recess 36 and serves to minimize fluid stagnation.

Each of couplings 16, 18 and 20 are fabricated substantially identical to the other with the exception that the external and internal diameter of each coupling is different to accommodate attachment to tubing having a corresponding internal diameter. Each of couplings 16, 18 and 20 is shown herein as having different diameter to accommodate tubings of corresponding diameters. Thus, the great flexibility accommodated by connector 10 is emphasized. Although three different sizes of couplings are shown (couplings 16, 18 and 20) any other suitably sized couplings (not shown) could also be bonded to the union to provide other variations for connector 10. Since each coupling is very similar in construction, only coupling 16 will be discussed in detail with the understanding that similar features will also be found on each of couplings 18 and 20.

Coupling 16 includes an adapter 40 having an external diameter configured to be received in a press-fit relationship by any of the standardized fittings 26, 32 or 34. A ring 44 is spaced from adapter 40 and is diametrally enlarged so as to form a collar. The ring 44 normally abuts the periphery of fitting 26.

The abutment surface of ring 44 may have a raised ridge 46 concentric therewith. Ridge 46 serves as an energy director for sonic energy when the coupling 16 is welded to body 12 using an ultrasonic welder. If desired, ridge 46 may be eliminated from the design and coupling 16 may be bonded to body 12 by other suitable non-pathogenic bonding agent. Coupling 16 includes a smoothly contoured inner lip 42 interiorly of adapter 40, the smooth contour serving to present a smooth flow profile to blood passing between coupling 16 and body 12 or cover 14. Thus, hemolysis is minimized when blood is passed through the connector 10.

A raised boss 48 is preferentially included on coupling 16 and is suitably imprinted with the size of tubing which coupling 16 is adapted to receive. This feature assists personnel both in assembling and using the bifurcated connector 10 of this invention.

The tubing coupling portion of coupling 16 includes a plurality of annular ridges 50, 52 and 54. These ridges act to securely engage the internal surface of a tubing (not shown) so as to prevent accidental removal and to seal against leakage. Preferably ridge 50 is configurated with a leading face having a slope of about 15 degrees whereas each of ridges 52 and 54 have a slope of 30°as measured from a line parallel to the axis of coupling 16. The reverse face of each of the ridges is preferentially perpendicular to the axis.

The illustrated embodiment may, within the purview of this invention be modified to include any combination of coupling dimensions. Also, if desired, the cover 14 could be altered to accommodate more than two fittings.

THE METHOD

The method of the present invention includes forming a hollow tapered body 12 and a cover 14 for body 12. The cover 14 is adapted to be bonded to body 12 with a suitable glue or, preferably, it may be bonded by welding for example with an ultrasonic welder. Ultrasonic welding is enhanced by including an energy director 56 (FIG 2) which is a ridge extending as an annulus ring around the periphery of cover 14. The energy director 56 concentrates the ultrasonic energy into an annular ring coincident with energy director 56 thereby suitably bonding together the two juxtaposed surfaces of cover 14 and body 12 in the vicinity of energy director 56.

In this illustrated embodiment, cover 14 also includes energy directors 58 and 60 surrounding the periphery of fittings 32 and 34, respectively. Clearly, each of energy directors 58 and 60 could also readily be included on the opposing faces of couplings 18 and 20 similarly to energy director 46 on coupling 16. The final positioning of any of energy directors 46, 56, 58 or 60 is a matter of design choice and accordingly, representative placement of each is illustrated herein with the understanding that each may be just as readily included on the respective opposing face.

Each of the couplings 16, 18 and 20 may be suitably bonded into any one of the fittings 26, 32 and 34 with the diameter of the tubing coupling end being suitably pre-selected according to the particular requirements.

Referring particularly to FIG. 2, it will be seen that the body, cover and couplings of tubing connector 10 are assembled but not bonded together. Energy directors 56, 58, 60 and 46 of cover 14 and coupling 16 are each placed in abutting relationship to their respective facing surfaces prior to bonding. Accordingly, it is possible to assemble the various components into the configuration shown in FIG. 2 and thereafter selectively bond the components into a finished bifurcated tubing connector 10 using a conventional ultrasonic welder. Examples of the ultrasonic welders that have been found to be useful are the Model 460 Ultrasonic Welder sold by Branson of Danbury, Connecticut or the Model WS-600 Ultrasonic Welder by Deltasonic, Inc. of Hawthorne, California.

It should be particularly emphasized with reference to FIG. 2 that the connector 10 is shown prior to final assembly. Each of the component parts are placed in the appropriate juxtaposition prior to being welded with an ultrasonic welder (not shown). Accordingly, the opposing faces which will be ultimately bonded together according to the one presently preferred method of this invention are shown as being separated by the height of each respective energy director therebetween. Otherwise each respective part of connector 10 would be shown touching the other in a face-to-face contact.

Clearly, one practicing the present invention may selectively dispense with the ultrasonic welding method of bonding the various components of this invention and eliminate each of the energy directors 56, 46, 58 and 60. Bonding with other agents could then be substituted for the sonic welding step to bond the various components together.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by a U.S. Letters Patent is:

1. A tubing connector for joining discrete fluid streams into a single fluid stream comprising:
a union assembly comprising;
a hollow body having a fitting at a first end, the opening accommodating reception of a tubing coupling, the body flaring outwardly to a second end; and
a cover configured to mate with the second end of the body, the cover having at least two fittings, each fitting having a generally uniform size and configuration and accomodating reception of a coupling; and
couplings having an adapter at a first end dimensionally configured to mate with each of the fittings in the union assembly, at least one coupling having a preselected external diameter at a second end which is different from the external diameter at the second end of the other couplings to accommodate telescopic connection with tubes having at least two different internal diameters.

2. A tubing connector as defined in claim 1 wherein the hollow body comprises a smoothly contoured interior surface.

3. A tubing connector as defined in claim 1 wherein the cover comprises a planar surface having two spaced fittings to thereby support two couplings in side-by-side parallel relationship.

4. A tubing connector as defined in claim 1 wherein the cover comprises an inwardly directed protrusion projecting to the interior of the body between the fittings so as to minimize fluid stagnation.

5. A tubing connector for joining two discrete fluid streams into a single stream comprising:
a plurality of modular couplings having a range of coupling dimensions so as to securely mate with tubes having a variety of dimensions, each of the modular couplings comprising an adapter of standardized dimension and configuration;
a contoured body comprising one enlarged end and another diametrally reduced end, the diametrally reduced end comprising a fitting; and
a cover for the one enlarged end of the body, the cover comprising at least two fittings and each of the fittings in the cover and body having a standardized dimension and configuration to receive any one of the plurality of modular couplings.

6. A method of assembling a bifurcated tubing connector comprising the steps of:
obtaining a hollow, tapered body, the body tapering from an enlarged opening at a first end to a fitting at the second end;
enclosing the enlarged opening of the body with a cover, the cover having two fittings, each fitting having the same diameter as the fitting of the body;
placing a tubing coupling in each of the fittings, each tubing coupling being configured to telescopically mate with a tubing having a preselected internal diameter; and
bonding together the body, cover and couplings into a bifurcated tubing connector.

7. A method of producing a bifurcated tubing connector for joining tubes, at least two of which have different coupling dimensions comprising the steps of:
obtaining a connector body which narrows from an enlarged end to a smaller end, the enlarged end having a cover thereon;
providing a single fitting in the body and at least two fittings in the cover each of the fittings having a uniform dimension and configuration;
fabricating a plurality of modular couplings having a range of coupling dimensions, each coupling having an adapter of standardized dimension and configuration so as to accomodate mounting upon the fittings;
selecting from among the modular couplings a combination of sizes required to join tubing of predetermined diametral dimensions; and
mounting the couplings in the fittings at desired fitting locations.

* * * * *